US006814968B1

(12) United States Patent
Graham et al.

(10) Patent No.: US 6,814,968 B1
(45) Date of Patent: Nov. 9, 2004

(54) INHIBITION OF VIRAL INFECTION AND SPREAD WITH VIRAL AND RHOA-DERIVED PEPTIDES

(75) Inventors: Barney Scott Graham, Nashville, TN (US); Manoj Pastey, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/129,565

(22) Filed: Aug. 5, 1998

Related U.S. Application Data

(60) Provisional application No. 60/087,955, filed on Jun. 4, 1998.

(51) Int. Cl.[7] .............................................. A61K 39/00
(52) U.S. Cl. ................................ 424/192.1; 424/211.1; 530/350; 530/300; 530/324; 530/395; 514/2
(58) Field of Search ................................ 530/350, 324, 530/395, 300; 514/12, 2; 435/196, 252.3; 424/192.1, 211.1

(56) References Cited

U.S. PATENT DOCUMENTS 6,060,297 A  *  5/2000  Hillman et al. ............. 435/196

FOREIGN PATENT DOCUMENTS

WO          WO 96/11019          4/1996

OTHER PUBLICATIONS

"Priming with Secreted Glycoprotein G of Respiratory Syncytial Virus (RSV) Augments Interleukin–5 Production and Tissue Eosinophilia after RSV Challenge", *Journal of Virology*, Apr. 1998, p. 2871–2880.
"AIDS Experts Testing More–Aggressive Antiviral Regimens", by William Check, *ASM News*, vol. 64, No. 4, 1998.
"AIDS Researchers Negotiate Tricky Slopes of Science", *Science*, vol. 280, May 8, 1998.
"Identification of a Reservoir for HIV–1 in Patients on Highly Active Antiretroviral Therapy", *Science*, vol. 278, Nov. 14, 1997.
"Induction of System and Mucosal Immune Responses to Human Immunodeficiency Virus Type 1 by a DNA Vaccine Formulated with QS–21 Saponin Adjuvant via Intramuscular and Intranasal Routes", *Journal of Virology*, Jun. 1998, p. 4931–4939.
"A Peptide Mimic of a Protective Epitope of Respiratory Syncytial Virus Selected from a Combinatorial Library Induces Virus–Neutralizing Antibodies and Reduces Viral Load in Vivo", *Journal of Virology*, Mar. 1998, p. 2040–2046.

"Rho GTPases and the Actin Cytoskeleton", *Science*, vo. 279, Jan. 23, 1998.
"Heptad Repeat Sequences Are located Adjacent to Hydrophobic Regions in Several Types of Virus Fusion Glycoproteins", *Journal of General Virology*, 71, p. 3075–3080.
"Revealing HIV's T Cell Passkey", *Science*, vol. 280, Jun. 19, 1998.
"The HIV–1 Envelope Glycoproteins: Fusogens, Antigens, and Immunogens", *Science*, vol. 280, Jun. 19, 1998.
"Progress in the Development of an HIV–1 Vaccine", *Science*, vol. 280, Jun. 19, 1998.
"HIV–1 Regulatory/Accessory Genes: Keys to Unraveling Viral and Host Cell Biology", *Science*, vol. 280, Jun. 19, 1998.
"The Small GTPase Rho: Cellular Functions and Signal Transduction", *J. Biochem*, vol. 120, No. 2, 1996.
"Arginine–Glycine–Aspartic Acid–Specific Binding by Foot–and Mouth Disease Viruses to the Purified Integrin $\alpha v \beta 3$ in Vitro", *Journal of Virology*, Nov. 1997, p. 8357–8361.
"Glycoprotein D of Herpes Simplex Virus (HSV) Binds Directly to HVEM, a Member of the Tumor Necrosis Factor Receptor Superfamily and a Mediator of HSV Entry", *Journal of Virology*, Aug. 1997, p. 6083–6093.
"Requirements for Different Components of the Host Cell Cytoskeleton Distinguish Ecotropic Murine Leukemia Virus Entry via Endocytosis from Entry via Surface Fusion", *Journal of Virology*, Oct. 1997, p. 7145–7156.
Niiro et al., "Up–regulation or rho A and rho–kinase mRNAs in the rat myometrium during pregnancy," *Biochem. Biophys Res. Comm.*, 230(2):356–359, 1997.
Nishimura et al., "Expression of rho A and rho kinase mRNAs in porcine vascular smooth muscle," *Biochem. Biophys Res. Comm.*, 227(3):750–754, 1996.
Pastey et al., "RhoA interacts with the fusion glycoprotein of resipratory syncytial virus and facilitates virus–induced syncytial formation," *J. Virology*, 73(9):7262–7270, 1999.

* cited by examiner

*Primary Examiner*—Laurie Scheiner
(74) *Attorney, Agent, or Firm*—Fulbright & Jaworski

(57) ABSTRACT

Isolated peptides, peptidomimetics, and antibodies which bind to the viral fusion protein binding domain of the RhoA protein or the RhoA binding domain of a viral fusion protein are useful for inhibiting infection in susceptible cells, in vitro and in vivo. Among these viruses are the Paramyxovirus respiratory syncytial virus (RSV) and the Lentivirus human immunodeficiency virus (HIV).

2 Claims, 3 Drawing Sheets

INHIBITION OF VIRAL INFECTION AND SPREAD WITH VIRAL AND RHOA-DERIVED PEPTIDES

This application claims benefit of now abandoned Provisional U.S. Patent Application Ser. No. 60/087,955 filed Jun. 4, 1998, entitled "Inhibition of Paramyxovirus and Lentivirus Infection and Spread with RhoA-Derived Peptides."

STATEMENT OF GOVERNMENT RIGHTS

A portion of the work described herein was funded in part by National Institutes of Health Grant Number RO1-AI-33933. The U.S. Government may therefore have certain rights relating to this invention.

BACKGROUND OF THE INVENTION

1. Field of the Invention

The present invention relates to methods of inhibiting viral entry and spread in vivo and in vitro. The invention further relates to isolated peptides from a mammalian Rho protein which have been found by the inventors to be useful for inhibiting entry of enveloped viruses, specifically paramyxoviruses and lentiviruses, into susceptible cells. In particular embodiments, the invention also relates to methods of preventing infection by enveloped viruses. These methods utilize the inhibitory effect of specific RhoA peptides or specific peptides isolated from the fusion glycoproteins of respiratory syncytial virus (RSV) or human immunodeficiency virus (HIV) on the viral entry mechanism of enveloped viruses.

2. Description of the Related Art

Paramyxoviruses and lentiviruses are important agents of clinical and veterinary disease. These viruses include important human pathogens such as respiratory syncytial virus (RSV), parainfluenza viruses, measles, mumps, HIV-1 and HIV-2, and veterinary pathogens such as bovine RSV, turkey rhinotracheitis virus, Newcastle's disease virus, rinderpest virus, canine distemper virus, the new morbilliviruses described in seals and horses, and simian immunodeficiency virus (SIV).

The major cause of serious lower respiratory tract illness in infants and immunosuppressed individuals is a paramyxovirus known as respiratory syncytial virus (RSV). Worldwide, RSV causes 65 million infections and 1 million deaths annually. The greatest incidence of disease from RSV infection is from 6 weeks to 6 months of age, with approximately 90,000 children hospitalized each year in the United States with infections caused by RSV. 4500 of those children die. Exaggerated RSV IgE response during RSV bronchiolitis in infancy has also been associated with the widespread problem of recurrent wheezing in early childhood.

Reinfections with RSV are more frequent than with most other viruses of the respiratory tract. Serious disease is usually associated with the first or second infection. Although disease severity declines with repeated infection, previous infection with RSV does not prevent illness in subsequent infections. Immunity is apparently incomplete. Live virus vaccines have generally proven to be inadequately immunogenic by the time they have been attenuated to a sufficient level to produce no clinical illness. A formalin-inactivated vaccine developed in the 1960s not only failed to produce a protective response against the virus, but induced exacerbated disease in vaccinated children during a subsequent epidemic, and some attenuated RSV strains have the potential to revert to virulence after human passage. Vaccine development has therefore been approached cautiously, although efforts to prevent RSV disease in infants and young children have continued to target active immunization with an inactivated vaccine, a live attenuated virus vaccine, or a subunit vaccine, and passive immunization of the fetus by active immunization of the mother with a human monoclonal RSV antibody or hyperimmune RSV immune globulin.

High-risk infants are treated with immunoglobulin (IG) to protect against RSV, but intravenous RSV IG is very expensive and administration requires a monthly infusion lasting 7 hours or more to maintain acceptable antibody titers.

While RSV poses a serious health threat, a more deadly infection is established by the lentiviruses known as human immunodeficiency viruses HIV-1 and HIV-2, which cause acquired immunodeficiency syndrome (AIDS). The World Health Organization estimates that 16,000 new HIV-1 infections in humans occur daily. Although some individuals have been identified in whom the infection has progressed slowly, the fatality rate for infected individuals is considered to be 100 percent.

Vaccine development for the prevention of HIV infection, and subsequent development of acquired immunodeficiency syndrome (AIDS), has been less successful than had earlier been anticipated. The present generation of gp120 subunit vaccines have not been shown to induce relevant antibody or cell-mediated immune responses of significant potency, and their performance in Phase I/II trials has been disappointing. Contributing to the difficulties in vaccine development are the characteristics of the virus, including poor immunogenicity of the HIV envelope glycoproteins and their resistance to neutralizing antibodies, the extensive variation in the viral genome, and the ability of the virus to become integrated into the host genome of immune cells (Agosto et al.).

One of the most promising, although very costly ($10,000 to $12,000 per year), treatments for HIV infection is known as highly active antiretroviral therapy (HAART), which combines the effects of nucleoside reverse transcriptase inhibitors and protease inhibitors. Even with this very aggressive treatment regimen, however, unintegrated HIV-1 DNA in cells from patients receiving HAART treatment has been found, suggesting that a low level of viral replication may continue and contribute to the maintenance of a reservoir of HIV-infected cells (Chun et al.).

Blocking the binding of the virus also has proven to be more difficult than anticipated. Early experiments had shown that HIV's primary receptor, CD4, was not itself sufficient to promote viral entry into a susceptible cell. Subsequently, coreceptors were identified, making earlier hopes to develop drugs to block viral attachment more difficult to realize. To date, more than a dozen chemokine receptor coreceptors for HIV gp120 have been found (Balter). The type of receptor used may even vary during the course of the viral infection (Owen et al.).

Identification of a specific fusion receptor could lead to the development of a more effective method of inhibiting HIV infection than have previous efforts to inhibit HIV infection by means of an attachment receptor, and inhibition of RSV infection via a specific fusion receptor provides a safer, more effective means of disease prevention than current vaccine and treatment techniques.

SUMMARY OF THE INVENTION

The present invention seeks to overcome these and other shortcomings inherent in the prior art by use of isolated peptides which inhibit viral infection of a susceptible cell. In the present invention, isolated peptides are derived from the mammalian RhoA protein sequence. More specifically, these peptides represent amino acid sequences within, and overlapping N-terminal and C-terminal to, the viral fusion protein binding domain of the RhoA protein. The RhoA viral fusion protein binding domain of the present invention is defined generally by amino acids 67–109 of the RhoA protein, with a core binding sequence located at residues 80–89. Furthermore, these peptides include, but are not limited to, a peptide comprising amino acid residues 77–95 of the RhoA protein.

Also provided by the present invention are peptides corresponding to amino acid sequences within, or overlapping N-terminal or C-terminal to, the RhoA binding domain of a viral fusion protein. These peptides may be defined by amino acid sequences from the F glycoprotein of respiratory syncytial virus, the gp41 fusion protein of human immunodeficiency virus, or the fusion proteins of other viruses which utilize a RhoA-mediated mechanism of cellular entry. The peptides include an isolated peptide corresponding to amino acids 35 to 50 of the human immunodeficiency virus glycoprotein, gp41, and an isolated peptide corresponding to amino acids 9 to 18 of the F1 subunit of the F glycoprotein of respiratory syncytial virus.

In the method of the present invention, isolated RhoA peptides and/or isolated viral fusion protein peptides are administered to a subject to inhibit viral infection by enveloped viruses, including respiratory syncytial virus and human immunodeficiency virus. Because these and other viruses, particularly the enveloped viruses, share a common cellular entry mechanism—fusion of the viral envelope and the cell membrane—the RhoA peptides inhibit viral entry for other viruses which are demonstrated to share the cellular entry mechanism common to respiratory syncytial virus (RSV) and human immunodeficiency virus (HIV).

Peptides of the present invention are administered in therapeutically effective dosages to a subject at risk for viral infection or a subject in whom active infection has already been established. In the subject at risk for infection, the peptides inhibit viral entry into susceptible cells and subsequent infection. In the subject in whom active infection has been established, the peptides inhibit cell-to-cell spread of virus and subsequent infection of additional cells.

Peptides, antibodies, and mimetic or peptidomimetic/peptoid compounds of the present invention are delivered by various routes, including, but not limited to, intravenously, orally, nasally, parenterally, and topically. More specifically, topical administration may include a liquid preparation for administration to a puncture wound, such as a needle prick, or cut. Topical administration may also include spermicidal or microbicidal jelly, to which the peptide, mimetic or peptidomimetic/peptoid of the present invention has been added, for use during sexual intercourse. Oral administration may include peptide complexed with a pharmaceutically acceptable carrier and delivered in tablet, caplet, or capsule form. More specifically, to protect the tissues of the intestinal mucosa, peptides, mimetics, or peptidomimetics/peptoids may be administered in enteric-coated capsules, caplets, or tablets. Oral administration also may include administration by aerosol spray or mouthwash, when peptide, mimetic or peptidomimetic/peptoid has been combined with a pharmaceutically acceptable carrier. Peptides, mimetics, or peptidomimetics/peptoids of the present invention may also be administered nasally, by nasal drops or nasal spray.

RhoA peptides, or viral fusion protein peptides as described by the present invention, in combination with appropriate immunogenic adjuvants, are administered to a subject at risk for viral infection to produce antibodies which inhibit viral infection. Anti-RhoA peptide antibodies and anti-viral fusion protein peptide antibodies also provide a means of passive immunization for individuals, such as very young children and immunosuppressed individuals, at increased risk of viral infection following exposure. Anti-idiotypic antibodies generated by peptides of the present invention also inhibit infection, as well as providing appropriate probes to determine antibody titers in immunized individuals.

RhoA peptides also may be used to identify the RhoA binding region of viral fusion proteins. Isolated peptides from these viral proteins are used as immunogens in vaccines to produce antibodies to inhibit viral infection in the immunized subject.

RhoA peptides, antibodies, and anti-idiotypic antibodies of the present invention can be used to screen blood and tissue samples for the presence of virus, as well as identify viruses which bind to the RhoA protein and are therefore likely to be susceptible to the inhibitory effects of the Rho or viral fusion peptides, antibodies, mimetics, or peptidomimetics/peptoids. The peptide, and anti-RhoA peptide antibodies, provide a rapid screening method for identifying other viruses for which the peptide will provide inhibition of viral infection in the manner that has been demonstrated for both respiratory syncytial virus and for human immunodeficiency virus. In the case of a subject infected with an unidentified viral agent, the peptide and anti-RhoA antibodies provide a rapid screening method for determining whether the viral agent will be inhibited by treatment with the RhoA peptide, viral fusion peptide, anti-RhoA peptide antibody, anti-viral fusion protein peptide antibody, mimetic, peptidomimetic, or peptoid.

RhoA peptides of the present invention are produced by means not limited to solid-phase synthesis and recombinant DNA methods. Peptidomimetic, peptoid mimetic, and other compounds which imitate the inhibitory efects of RhoA and viral fusion peptides are produced using solid phase and non-solid phase combinatorial methods, and identified using screening methods including, but not limited to high-throughput screening by ELISA, by size exclusion chromatography (when bound to the appropriate RhoA or viral fusion protein target), and by phage display library screening methods.

DETAILED DESCRIPTION OF THE PREFERRED EMBODIMENTS

Figure 1:
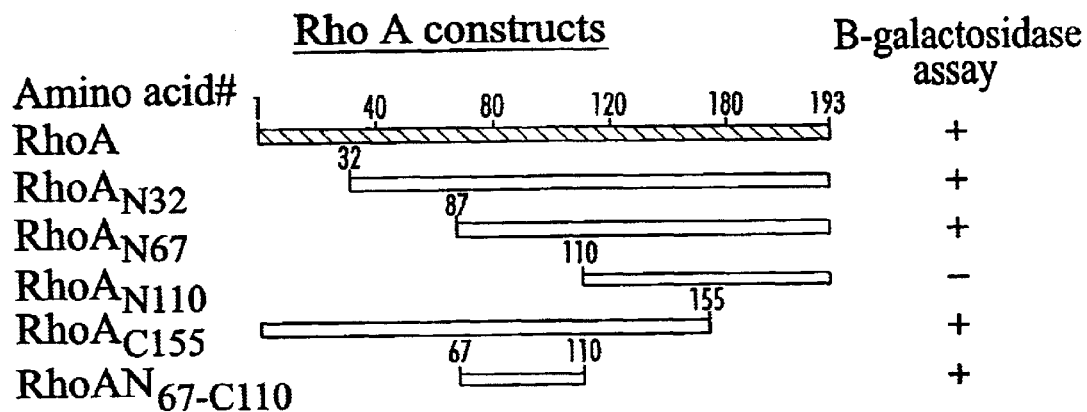
FIG. 1 describes the sequences of RhoA peptides used in inhibition assays to isolate the RhoA peptides which inhibit viral infection in vivo and in vitro.

It is important to an understanding of the present invention to note that all technical and scientific terms used anywhere herein, unless otherwise defined, are intended to have the same meaning as commonly understood by one of ordinary skill in the art; that techniques employed herein are also those that are known to one of ordinary skill in the art, unless stated otherwise; and that publications mentioned herein are incorporated by reference.

It is also important to note that reference to particular protein and DNA sequences is not intended to be limiting, but should be read to include all such related materials that one of ordinary skill in the art would recognize as being of interest or value in the particular context in which that discussion is presented. A biomolecule may be produced that is structurally related to or derived from the stated material. A biomolecule may also be produced for use in a different but known procedure to achieve the same goals as those to which the use of a suggested method, material or composition is directed. All such substitutions and modifications as are known to those of skill in the art are included within the scope of the present invention.

It should be further noted that the scope of the present invention is not limited to full-length sequences of each of the nucleic acid or amino acid sequences described. It is well understood by those of skill in the art that subfragments of sequences may be prepared, and that those subfragments retain some or all of the biological acitivity of the full-length sequences. Such subfragments are included within the scope of this invention. Previous efforts to prevent and treat viral infection, particularly viral infection by lentiviruses and paramyxoviruses, have concentrated on inactivation of the virus by immune response to viral antigens or on inhibition of binding of virus to cellular receptors. These efforts have been unsuccessful primarily because the vaccines have failed to elicit an appropriate immune response and the use of multiple cellular receptors allows a virus to thwart most efforts to inhibit receptor binding. The present invention is directed to a method of using isolated peptides from a cellular protein, or viral fusion protein which specifically interacts with the cellular protein, to inhibit viral infection in vivo and in vitro. The inventors have demonstrated that isolated peptides, whose sequences are derived from the sequence of the RhoA protein, inhibit viral entry and infection of cells by enveloped virus members of diverse viral families. These viruses have previously been shown to share a common cellular entry mechanism. It is therefore expected that the peptides, antibodies derived therefrom, and peptidomimetic or other functionally equivalent molecules of the present invention will have inhibitory effects on viral entry and infection by a number of viruses which share a common cellular entry mechanism with the viruses described herein.

As used in this specification, "inhibitory peptides" comprise isolated peptides representing the viral fusion protein binding domain of the RhoA protein and isolated peptides representing the RhoA binding domain of viral fusion proteins, particularly respiratory syncytial virus glycoprotein F1 and human immunodeficiency virus glycoprotein gp41.

Inhibitory Peptides Derived from the RhoA Protein Sequence

RhoA is a member of a family of small G proteins associated with actin polymerization and activation of protein kinase C and phospholipase D. The Rho family is part of the Ras superfamily of small GTP-binding proteins, and consists of Rho (A, B, and C), Rac (1 and 2), two Cdc42 isoforms, RhoD, RhoE, RhoG, Tc10 and TTF (Ridley). Rho has been proposed to act as a molecular switch to control a signal transduction pathway that links membrane receptors to the cytoskeleton (Hall). Rho activation leads to the assembly of contractile filaments (actin-myosin stress fibers) and associated focal adhesion complexes (Machesky et al.), and Rho has also been shown to promote integrin clustering in the cell membrane (Machesky et al.).

RhoA activation has been associated with membrane fusion events, and the actin cytoskeletal network has been demonstrated to play a critical role in viral entry mechanisms. A direct or indirect role for the Rho proteins in viral entry has, however, not previously been demonstrated.

In the present invention, the inventors determined that the addition of whole RhoA protein to RSV prior to infection of HEp-2 cells increased the number and size of plaques in cell culture, suggesting that RhoA is involved in membrane fusion events leading to viral infection of the cell. Overexpression of RhoA in transfected HEp-2 cells increased the number and rate of syncytium formation after RSV infection, while cells treated with *Clostridium botulinum* C3 exotoxin, which specifically ADP riboxylates and inactivates RhoA, exhibit reduced RSV syncytium formation, suggesting a role for RhoA in the process of cell-to-cell spread of RSV. Immunofluorescence stains have shown that uninfected cells in the presence of RSV infected cells up-regulate RhoA expression. Cells treated with C3 also demonstrated reduced syncytium formation induced by parainfluenza virus type III (PIV3), indicating that RhoA may play a fundamental role in the membrane fusion process of other enveloped viruses and not be limited to interactions with RSV alone.

The RhoA protein comprises a protein of 193 amino acid residues. The sequence may be obtained through GenProt accession number 68960PID g68960. Using the yeast two-hybrid system, the inventors have identified a viral fusion protein binding domain in RhoA which specifically binds to RSV F glycoprotein (Pastey et al.). This domain comprises approximately 43 amino acid residues in the region of amino acid residues 67–109 of the RhoA protein. The binding domain of RhoA was then further defined using three overlapping 19 amino acid peptides (RhoA$_{67-85}$, Rho$_{77-95}$, and RhoA$_{87-105}$), three 10 amino acid peptides (RhoA$_{77-86}$, RhoA$_{80-89}$, and RhoA$_{83-92}$) and five 4 amino acid peptides (RhoA$_{77-80}$, RhoA$_{78-81}$, RhoA$_{79-82}$, RhoA$_{80-83}$, and RhoA$_{81-84}$) which spanned the 43 amino acid sequence shown to bind RSV F glycoprotein. Addition of the peptide comprising the sequence of amino acids 77–95 (RhoA$_{77-95}$) was subsequently shown to inhibit plaque formation when incubated with RSV before adding the suspension to a culture of HEp-2 cells. Subsequent experiments indicated that the peptide inhibited RSV in vivo when administered to mice, and that the same peptide inhibited both infection and syncytia formation by HIV in cultured MT-2 cells and parainfluenza virus (PIV) cultured in HEp-2 cells. In further experimentation, the inventors determined that RSV entry into susceptible cells is also inhibited by a smaller peptide (10 amino acids) comprising amino acid residues 80–89 of the RhoA protein sequence.

Other Rho family proteins, particularly RhoC, which shares 92% sequence homology with RhoA, and RhoB, which shares 85% sequence homology with RhoA (Drivas et al.), may also be involved in viral entry mechanisms. Therefore, it is expected that other Rho family proteins may be involved in the viral membrane fusion mechanism, and peptides isolated from the sequence of these proteins may produce inhibitory effects similar to those produced by the peptides of the RhoA protein in the present invention.

Inhibitory Peptides Isolated from Viral Fusion Glycoproteins

In respiratory syncytial virus, the F glycoprotein (RSV F) serves the fusion function. Monoclonal antibodies that precipitate the 68- to 70-kD F glycoprotein inhibit cell-to-cell fusion normally caused by RSV. In HIV, the transmembrane glycoprotein gp41 (HIV gp41) mediates membrane fusion between viral and host cell membranes, thereby depositing the viral core into the cytoplasm. A leucine zipper-like heptad repeat sequence has been shown to be conserved between both RSV F and HIV gp41 membrane fusion proteins, as well as a number of other viruses (Chambers et al.). Proline substitution for any of the conserved leucine or isoleucine residues located in the leucine zipper-like heptad repeat sequence of HIV-1 gp41 renders the virus noninfectious and the envelope protein unable to mediate membrane fusion (Chen et al.), indicating a possible role for this conserved sequence motif in a common viral fusion mechanism. The inventors have now demonstrated that isolated peptides derived from a RhoA protein sequence defined as the RSV F binding domain inhibit the membrane fusion activities of both RSV F and HIV gp41, as indicated by inhibition of viral entry and infection of susceptible cells. Isolated peptides derived from the RhoA protein binding domain of RSV F and HIV gp41 provide the same inhibitory function, blocking the fusion protein/RhoA binding, that RhoA peptides provide. Furthermore, antibodies to these isolated peptides, specific for the binding region, also provide the same inhibitory function that anti-RhoA peptide antibodies provide.

Antibodies of the present invention include antibodies raised against any of the peptides mentioned above, as well as anti-idiotypic antibodies produced against anti-peptide antibodies.

The fusion glycoprotein (F glycoprotein) of RSV is synthesized as a single protein molecule, which is subsequently enzymatically cleaved to form two subunits—F1 and F2. The two subunits form a single fusion glycoprotein, being held together by disulfide linkages. Yeast transformed with various N-terminal and C-terminal deletion mutants of the RSV F glycoprotein (see FIG. 3) and screened by β-galactosidase assay for interaction with the RhoA protein indicated that the RhoA binding domain of the F glycoprotein of RSV is located between amino acids 146 to 155. This corresponds to amino acids 9 to 18 of the F1 subunit of the RSV fusion glycoprotein.

HIV-1 gp41 N-terminal deletion mutants were used to determine the location of the RhoA binding domain of the HIV-1 fusion glycoprotein, gp41. Only yeast cotransformants with the gp41N29 deletion mutant showed interaction with the RhoA protein as assayed by β-galactosidase assay, indicating that the binding domain is contained within and overlapping the region between amino acids 29 and 45 of HIV gp41 or amino acids 540 to 556 of HIV gp160.

Peptides and antibodies of the present invention have been shown to have inhibitory effect against viral entry and infection of both RSV and HIV. This effect has been determined to exist both in vitro and in vivo. In both viruses the RhoA binding domain has been determined to be located between the hydrophobic amino terminus and the highly conserved heptad repeat region. Because a number of diverse viral families utilize common fusion mechanisms and fusion sequence motifs, it is expected that the peptides and antibodies of the present invention will have inhibitory effect against other viruses as well as RSV and HIV.

The peptides and antibodies described by the present invention have multiple uses, both in vivo and in vitro, some of which are described below.

Antibodies and Immunoassays

Antibodies, mimicking the inhibitory effect of the RhoA inhibitory peptide, both polyclonal and monoclonal, specific for isoforms of antigen may be prepared using conventional techniques, as will be generally known to those of skill in the art. Briefly, a polyclonal antibody is prepared by immunizing an animal with an immunogen comprising a peptide representing the viral fusion protein binding region of RhoA, or a peptide representing the RhoA binding region of a viral fusion protein, such as the RhoA binding region of RSV F, and collecting antisera from the immunized animal. Typically an animal used for production of antisera is a non-human animal including rabbits, mice, rats, hamsters, pigs, goats or horses. Because of the relatively large blood volume of rabbits, a rabbit is a preferred choice for production of polyclonal antibodies. An antibody can be a polyclonal or a monoclonal antibody. In a preferred embodiment of the present invention, an antibody is a monoclonal antibody. Methods for preparing and characterizing antibodies are well known in the art, and polyclonal antisera may be obtained, after allowing time for antibody generation, simply by bleeding the animal and preparing serum samples from the whole blood.

It is proposed the monoclonal antibodies of the present invention will find useful application in standard immunochemical procedures, such as ELISA and Western blot methods and in immunohistochemical procedures such as tissue staining, as well as in other procedures which may utilize antibodies specific to the RhoA binding region of a viral fusion protein. In general, both polyclonal and monoclonal antibodies against the RhoA binding region of a viral fusion protein may be used in a variety of embodiments. For example, they may be used to identify other viruses which bind the RhoA viral fusion protein binding region, and which may be expected to be inhibited by the RhoA inhibitory peptide. They may also be used to detect the presence of virus in a blood or tissue sample.

Although the Rho A binding region of a viral fusion protein is immunogenic, as demonstrated by its ability to stimulate polyclonal antibody production, a given composition may vary in its immunogenicity. It is often necessary to boost the host immune system, which may be accomplished by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin may also be used as carriers. Methods for conjugating peptides and polypeptides to a carrier protein are well known in the art and include linking to glutaraldehyde, m-maleimidobencoyl-N-hydroxysuccinimide ester, carbodiimide and bis-biazotized benzidine.

Immunogenicity of a particular immunogen composition can be enhanced by the use of non-specific stimulators of the immune response, known in the art as adjuvants. Exemplary and preferred adjuvants include complete Freund's adjuvant, incomplete Freund's adjuvants and aluminum hydroxide adjuvant.

The amount of immunogen composition used in the production of polyclonal antibodies varies based upon the nature of the immunogen as well as the animal used for immunization. A variety of routes can be used to administer the immunogen (subcutaneous, intramuscular, intradermal, intravenous and intraperitoneal). Methods of determining immunogen dosages and routes of administration are known to those of skill in the art and may be determined with a limited degree of experimentation.

Monoclonal antibodies may be readily prepared with well-known techniques, such as those exemplified in U.S. Pat. No. 4,196,265, incorporated herein by reference. Typically, this technique involves immunizing a suitable animal with a selected immunogen composition. In the method of the present invention, the immunogen would be a peptide representing the RhoA binding region of a viral fusion protein, such as RSV F or HIV gp41. The immunogen, along with adjuvant, if needed, is administered in a manner effective to stimulate antibody producing cells. Rodents such as mice and rats are preferred animals, although rabbits, sheep, and frogs may also be used. Mice are the hosts of choice, with the BALB/c mouse being preferred, since it routinely has been shown to provide a higher percentage of stable cell fusions.

Following immunization, somatic cells which have the potential for producing antibodies, specifically B-lymphocytes, are selected for use in the monoclonal antibody (mAb) protocol. B-lymphocytes (B cells) may be obtained from biopsied spleens, tonsils, or lymph nodes, or from a peripheral blood sample. Spleen cells and peripheral blood cells are preferred, with spleen cells preferred because they provide an abundant source of antibody-producing cells in the dividing plasmablast stage. Typically, a spleen from an immunized mouse contains approximately $5 \times 10^7$ to $2 \times 10^8$ lymphocytes. Peripheral blood cells are preferred because peripheral blood is easily accessible.

The antibody-producing B cells are then fused with cells of an immortalized myeloma cell to produce hybridomas. Generally, the myeloma cell chosen is one of the same species as the animal that was originally immunized. Myeloma cell lines suited for use in hybridoma-producing fusion procedures preferably are non-antibody-producing, have high fusion efficiency, and enzyme deficiencies that make them incapable of growth in selective media. Use of selective media insures that the only cells surviving in the medium will be hybridomas, with the genetic capability of making proteins necessary for survival in the selective media imparted by the antibody-producing cell.

A number of myeloma cells are known to those of skill in the art. If the immunized animal is a mouse, P3-X63/Ag8, Pe-X63-Ag8.653, NS1/1.Ag4 1, Sp210-Ag14, FO, NSO/U, MPC-11, MPC11-X45-GTG 1.7 and S194/5XXO Bu1 may be used. If the immunized animal is a rat, R210.RCY3, Y3-Ag 1.2.3, IR983F and 4B210 may be used.

It is proposed that RhoA peptides of the present invention will find utility as immunogens, not only in connection with vaccine development, but also in connection with immunoassays for detection of viruses in blood and tissue samples, as well as for detection of viruses which bind to RhoA during the cell membrane fusion process. Anti-RhoA peptide antibodies and anti-idiotypic antibodies will also find utility in the identification of viral fusion protein domains which bind to the RhoA protein.

Preferred immunoassays of the invention include a variety of enzyme linked immunosorbent assays (ELISAs) known to those of skill in the art. Other embodiments which will provide similar utility include radioiinmunoassays (RIAs) and other non-enzyme ked antibody binding assays or procedures.

In the ELISA assay, peptides incorporating RhoA amino acid sequences are immobilized onto a selected surface, preferably a surface exhibiting a protein affinity such as the wells of a polystyrene microtiter plate. After washing to remove incompletely adsorbed material, an antigenically neutral nonspecific protein such as bovine serum albumin (BSA) or casein may be coated onto the well in order to block nonspecific adsorption sites on the immobilizing surface and reduce the background caused by nonspecific binding of antisera onto the surface.

After binding of antigenic material to the well, coating with a non-reactive material to reduce background, and washing to remove unbound material, the immobilizing surface is contacted with the antisera or clinical or biological material to be tested in a manner conducive to complex (antigen/antibody or other complex) formation. These conditions include diluting the antisera with diluents such as BSA, bovine gamma globulin (BGG) and phosphate buffered saline (PBS)/Tween. These agents aid in reduction of nonspecific background. Layered antisera is allowed to incubate for 1 to 4 hours. Preferred incubation temperature range is 25–37° C.

Following incubation, the surface is washed to remove non-complexed material. Washing with a solution of PBS/Tween, or borate buffer, is a preferred washing procedure.

To provide a means for detection of the complex, a second antibody may be applied, having specificity for the first antibody, clinical, or biological compound applied. The second antibody will preferably have an associated enzyme which will generate the development of a detectable color (for colorimetric assay) when incubated with an appropriate chromogenic substrate. Quantification of complex formation is then determined by measuring the degree of color generation using, for example, a visible spectra spectrophotometer.

Synthetic Peptides

The present invention describes isolated peptides derived from the sequence of a viral fusion protein binding domain in a region of RhoA, roughly defined by amino acid residues 67 to 109. The invention also describes isolated peptides derived from the sequence of a viral fusion protein RhoA binding domain roughly defined by amino acid residues 9 to 18 in the F1 subunit of the RSV F glycoprotein and roughly defined by amino acid residues 29 to 50 of the HIV glycoprotein gp41. In various embodiments of the present invention, these peptides are relatively small in size, and can be synthesized in solution or on a solid support by techniques known to those of skill in the art. Automated synthesizers are commercially available. Known protocols include those published by Tam et al. and Merrifield. Short peptide sequences or libraries of overlapping peptides can be readily synthesized and screened using these methods.

Functionally Equivalent Amino Acids and Peptides

It is not uncommon for amino acid modifications in a peptide or protein to result in a molecule having like or otherwise desirable characteristics. For example, certain amino acids may be substituted for other amino acids in a protein structure in order to modify or improve its antigenic or immunogenic activity or binding affinity.

Kyte et al. have described the relative importance of the hydrophobicity or hydrophilicity of certain amino acids and their position in a protein or peptide. Based upon their discoveries, it has been found that certain amino acids may be substituted for other amino acids having a similar hydropathic index and still retain a similar biological activity. Preferred substitutions for monitoring binding capability will generally involve amino acids having index scores on the hydropathic index within ±2 units of one another. More preferable, these substitutions will involve amino acids having index scores within ±0.5 to ±1.0 unit.

Common substitutions which have been shown to result in similar biological activities include the substitution of leucine hydropathic index +3.8) for either valine (hydropathic index +4.2) or isoleucine (hydropathic index +4.5), or the substitution of lysine for arginine (hydropathic index −3.9 and −4.5, respectively).

U.S. Pat. No. 4,554,101, incorporated herein by reference, states that the greatest local average hydrophilicity of a protein, as governed by the hydrophilicity of its adjacent amino acids, correlates with its immunogenicity and antigenicity—with the biological properties of the protein.

Amino acid substitutions are generally based on the relative similarity of R-group substituents. Consideration is given to the similarities between size, electrophilic character, charge, and other properties of R-groups of substituted amino acids.

Peptide Production by Means of Recombinant DNA

The peptides described in the present invention may also be produced by means of recombinant DNA methods, using nucleotide sequences which correspond to the coding regions of the amino acid sequences of the desired peptides. The nucleotide sequence encoding the RhoA protein has been described (Yeramian et al.). Methods of protein expression utilizing recombinant DNA methods are well known to those of skill in the art, and include ligation of a nucleotide sequence encoding a peptide as described in the present invention into an appropriate expression vector. In a preferred embodiment, an appropriate expression vector provides a means for purifying the resulting recombinant protein. Such expression vectors are known to those of skill in the art, and may include a vector for the IMPACT system (New England Biolabs), which uses a protein splicing element known as an intein, modified to undergo a self-cleavage reaction at its N-terminal junction at 4° C. when induced by thiol reagents such as dithiothreitol (DTT). The nucleotide sequence encoding the target protein or peptide is inserted into the multiple cloning site of the IMPACT expression vector to create a fusion between the C-terminus of the target peptide and the N-terminus of the gene encoding the intein. Affinity purification is facilitated by a chitin binding domain, encoded by nucleotides added to the C-terminus of the intein. Purification of crude extracts of cells from an *E. coli* expression system are passed over a chitin column, followed by on-column cleavage to release the target peptide with a reducing agent such as DTT or 2-mercaptoethanol. Purification is performed at 4° C., eliminating the risk of destabilization inherent in higher temperature purification methods.

Alternately, the peptide may be produced by insertion of the nucleotide sequence into plasmid pGEX (Frangione, et al.) which accomplishes protein production and purification by producing a glutathione S-transferase fusion protein which can subsequently be cleaved by Factor X to produce a biologically active peptide or protein.

Peptidometics and Peptoids Selected from a Combinatorial Library

Another embodiment for the preparation of polypeptides according to the present invention is the generation of mimetic compounds. Mimetics are compounds that can mimic the critical features of the molecular recognition process of the peptide and reproduce the action of the peptide. A mimetic is expected to permit molecular interactions similar those of the natural molecule. While maintaining the functionalities and relative side-chain positions of the parent peptide, mimetics are likely to have improved pharmacokinetics in comparison with peptides. Morphine, for example, is a non-peptide peptidomimetic that mimics the opioid peptides. In the present invention, mimetic compounds can imitate the orientation of the amino acid side chains along the peptide backbone and possess many of the natural properties of the RhoA peptides, but with altered and often improved characteristics.

Peptoids are oligomers of N-substituted glycine residues. Modular build-up of peptoids facilitates the synthesis of numerous compounds targeted to produce the effects of naturally-occurring peptides.

Combinatorial libraries provide a method for identifying other compounds with structural and functional similarity to the inhibitory peptide of the present invention. Techniques known to those of skill in the art make it possible to screen thousands of compounds in one week. Combinatorial libraries may be generated by solid-phase synthesis, preferably using a resin scaffold, or may be generated by phage display or other methods known to those of skill in the art.

Methods for producing diverse peptide, peptidomimetic, or other mimetic populations and methods of screening these populations by phage display are well known in the art. Peptides or peptidomimetics of random sequence are displayed on bacteriophage, the phage are contacted with a target, and phage that interact with the target are isolated, recloned, and the sequences encoding the active peptides determined. Methods for preparing diverse populations of binding domains on the surface of a phage are, for example, described by Ladner et al., U.S. Pat. No. 5,223,409 (incorporated herein by reference). Ladner et al. describe methods for producing randomly or selectively mutated binding domains, selecting potential binding domains, and phage vectors useful for producing a phage display library.

Methods for producing phage peptide display libraries, including methods of diversifying the population of expressed peptides and appropriate vectors for phage display, are also described by Smith and Scott in *Meth. Enzymol.* 217: 228–257 (1993) and *Science* 249: 386–390 (1990), incorporated herein by reference. A codon-based mutagenesis method, which may be utilized with phage display technology, has been described by Huse, U.S. Pat. No. 5,264,563, incorporated herein by reference.

A method for generating combinatorial libraries is embodied in the chemical synthesis "mix-and-split," or "pool-and-divide" technology. With this technique, individual reactants are mixed in separate lots to provide a number of possible combinations. The resulting mixture is then split into equal parts, and subsequent chemical reactions provide more combinations of reactants. The number of compounds produced is therefore multiplicative, not additive as with standard methods. A random library of hexapeptides composed of the 20 naturally occurring amino acids can be synthesized in one reaction chamber and may yield as many as 64 million peptides.

Using the "split-synthesis" solid phase method, bead libraries can be generated so that each bead displays only one chemical entity. The "one-bead one-compound" combinatorial library can be assayed for specific binding to RhoA or to a viral fusion protein using either a solid-phase on-bead binding or functional assay, or a releasable solution phase assay.

The "one-bead one-compound" combinatorial library method has been used to discover peptides that bind to the cell surface immunoglobulins of murine lymphoma cells (Lam, et al.). This method uses amino-polyethylene glycol grafted polystyrene beads as the solid-phase support. In the case of peptide libraries, resins are first split into multiple aliquots, after which 4-fold excess of individual Fmoc-amino acids, together with coupling agents, such as HOBt and BOP are added. When the coupling reactions are completed the resins are mixed together, thoroughly washed, and the N-a-Fmoc group deprotected with 20% piperidine (v/v). The beads are washed thoroughly, split into several aliquots, and prepared for the next coupling cycle. After the desired number of coupling cycles, the N-a-Fmoc and side chain protecting groups are removed by treatment with piperidine, followed by treatment with trifluoroacetic acid (TFA). Peptides may stay attached to the bead, or, if resin with cleavable linkers is used, may be cleaved so that the peptide can be assayed in solution phase.

In a preferred screening method, a large library of target compounds is screened by adhering a target compound to a bead, in the manner described by Lam et al. (1991). The target compound, the RhoA protein or a viral fusion protein, is incubated with the compound library in concentrations of 500 pMol each. Incubation is performed at pH 7.0 in phosphate buffered saline with 1% DMSO for 1 hour. Unbound compounds are removed by size exclusion chromatography, and their identities analyzed by mass spectrometry. To identify compounds that bind specifically to the binding site, a second reaction mixture contains the target protein adhered to beads, the compound library, and an inhibitory peptide of the present invention (either a RhoA peptide or a peptide from a viral fusion protein). The inhibitory peptide is applied to the target protein first, followed by application of the compound library. Compounds that bind specifically to the binding site of the present invention, and will therefore inhibit viral infection in the manner of the peptides of the present invention, are those compounds that specifically are identified in the first reaction mixture but are not present in the second reaction mixture due to being inhibited from binding to the binding site by the presence of the inhibitory peptide.

A serial approach for screening such peptide libraries has been described by Houghten et al. in Nature 354: 84 (1991), incorporated herein by reference. Beutel, U.S. Pat. No. 5,670,326 (incorporated herein by reference), describes a method of screening libraries of compounds, such as nucleic acids or peptides, by contacting libraries with a target molecule to identify compounds which bind the target with the desired specificity.

A method for synthesizing and screening a combinatorial solid-phase peptide library to identify peptide mimotopes of a conserved epitope of RSV F protein has been described by Chargelegue et al., and is incorporated herein by reference. In this method, a solid-phase combinatorial peptide may be synthesized utilizing a scaffold, such as a polystyrene resin. In a preferred method, the library may be synthesized on Novasyn TG resin (Novabiochem, Nottingham, United Kingdom). Automated solid-phase synthesis methods are used to synthesize the peptides. These methods are known to those of skill in the art, and may include, in a preferred embodiment of the invention, 9-fluorenylmethoxycarbonyl (Fmoc) chemistry. Resin-bound peptides are treated with trifluoroacetic acid to deprotect the side chains while the peptides remain attached to the resin.

Peptides are also synthesized as linear free peptides by automated solid-phase synthesis. Solid-phase synthesis methods are known to those of skill in the art, and may include 9-fluorenylmethoxycarbonyl (Fmoc) chemistry. Peptide purity may be determined by reverse-phase high-pressure liquid chromatography and mass spectrometry.

In the method of the present invention, potential inhibitory compounds may be screened using the enzyme-linked immunosorbence assay (ELISA). 96-well or 384-well microplates are coated with ligand (RhoA or the viral fusion protein of RSV or HIV-1) at, for example, 5 mg/ml in sodium bicarbonate buffer overnight at 4° C., washed with water, and blocked with 200 ml, for example, of phosphate-buffered saline (PBS)-bovine serum albumin (BSA) 2.5% per well for 2 hours at 37° C. After plates have been washed, they are incubated with labeled peptides of the present invention and products from compound libraries to be screened. Potential inhibitory compounds within the library may be identified by measuring unbound labeled inhibitory peptides which have been competitively inhibited from binding to the appropriate binding domain on the viral fusion protein or RhoA protein.

Generally, peptides have a poor oral-bioavailability due to degradation in the digestive tract, as well as poor absorption in the digestive system. Peptides also may have a short duration of action because they are rapidly degraded by proteolytic enzymes in the blood and other tissues and fail to cross the blood-brain barrier. Peptidomimetics, peptoids, and other natural and synthetic compounds provide a means to circumvent these problems and provide the benefits of the inhibitory peptides and antibodies of the present invention for the therapeutic uses described below.

Design of Virus-specific and Broad Spectrum Antiviral Vaccines

An inhibitory peptide, mimetic or peptidomimetic/peptoid of the present invention provides an immunogen for the stimulation of antibodies which inhibit virus entry into susceptible cells. Such a molecule also provides an immunogen for stimulation of anti-idiotypic antibodies with binding specificity for the RhoA binding region of a viral fusion protein. Furthermore, the Rho binding region of a viral fusion protein provides an immunogen for a human or other mammalian subject to stimulate immunoglobulins which exhibit binding specificity equivalent to that of the RhoA inhibitory peptide, producing a similar inhibitory effect on viral entry into a susceptible cell. Alternately, peptides representing the viral fusion protein binding region of RhoA provide immunogens to stimulate immunoglobulins which exhibit binding specificity equivalent to that of the viral fusion protein peptides of the present invention. These immunoglobulins, by blocking the binding site on RhoA, produce an inhibitory effect on viral entry into a susceptible cell.

Methods for preparation of vaccines which contain peptide sequences as active ingredients are well known in the art. Such methods are exemplified in U.S. Pat. Nos. 4,578, 770; 4,596,792; 4,599,230; 4,599,231; 4,608,251; and 4,601,903, all incorporated herein by reference. Typically, such vaccines are prepared for injection into a human or mammalian subject. Injectable vaccines may be prepared as liquid solutions or suspensions. Solid forms may also be prepared which are suitable for solution in, or suspension in, liquid prior to injection. The preparation may also be emulsified. The active immunogenic ingredient is often mixed with a pharmaceutically acceptable carrier which is compatible with the active ingredient. Suitable carriers include, but are not limited to, water, dextrose, glycerol, saline, ethanol, and combinations thereof. The vaccine may contain additional agents such as wetting or emulsifying agents, pH buffering agents, or adjuvants which enhance the effectiveness of the vaccine.

The vaccine may be conventionally administered parenterally. Either subcutaneous or intramuscular injection is appropriate. Other modes of administration may include oral administration, nasal administration (particularly for RSV), rectal administration, and vaginal administration, which may involve combining the peptide immunogen with pharmaceutically acceptable carriers such as mannitol, lactose, starch, magnesium stearate, sodium saccharine, cellulose, magnesium carbonate, or other carrier. Compositions for oral administration may form solutions, suspensions, tablets, pills, capsules, sustained release formulations or powders. In a preferred embodiment, the composition forms an enteric-coated capsule for release of the peptide into the lumen of the intestine, particularly where the immunogen comprises an isolated peptide comprising amino acid residues of the RhoA binding region of HIV gp41 combined with a gp120 subunit immunogen.

The peptides of the present invention may be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, mandelic, oxalic, and tartaric. Salts formed with the free carboxyl groups may also be derived from inorganic bases such as, for example, sodium, potassium ammonium, calcium, or ferric hydroxides, and such organic bases as isopropylamine, trimethylamine, 2-ethylamino ethanol, and histidine.

Nucleic acids encoding the peptide or peptides may be incorporated into a recombinant vector, such as adenovirus, for administration.

The vaccine is administered in a manner compatible with the dosage formulation, and in such amount as will be therapeutically effective and immunogenic. The quantity to be administered depends on the subject to be treated, taking into account, for example, the capacity of the individual's immune system to synthesize antibodies, and the degree of protection desired. Precise amounts of active ingredient (peptide immunogen) to be administered depend on the judgment of the practitioner. Suitable dosage ranges generally require several hundred micrograms of active ingredient per vaccination. Also variable are regimes for initial administration and booster vaccinations, which should be determined by the judgment of the practitioner. Dosage of vaccine will depend on the route of administration and will vary according to the size of the host.

Adjuvants for use in combination with the peptide immunogen of the present invention for vaccination include, but are not limited to, aluminum hydroxide or phosphate, also known as alum, commonly used as 0.05 to 0.1 percent solution; aggregation of the protein in the vaccine by heat treatment with temperatures ranging between 70° for 30 seconds to 101° C. for 2 minutes.

It is important to note that the inhibitory peptides of present invention have been shown to have a significant inhibitory effect on primary isolates of HIV, as shown in Table 1. One obstacle to the treatment of HIV infection has been the fact that many potential treatments have shown effectiveness with HIV cultures, only to have no significant effect on primary isolates of the virus.

TABLE 1

Titers of Primary Isolates

| Sample | Peptide (5 μg/ml) | Mean Titer | S. D. |
|--------|-------------------|------------|-------|
| R8     | —                 | 34,600     | 624   |
|        | +                 | 120        | 106   |
| R8Bal  | —                 | 20,720     | 3,251 |
|        | +                 | 360        | 69    |
| 3076   | —                 | 140,133    | 15,602 |
|        | +                 | 4,133      | 1,665 |
| 3110   | —                 | 585,067    | 18,249 |
|        | +                 | 7,200      | 3,020 |
| 3105   | —                 | 9,613      | 1,044 |
|        | +                 | 213        | 129   |
| 3107   | —                 | 787        | 61    |
|        | +                 | 160        | 40    |
| 3109   | —                 | 2,253      | 467   |
|        | +                 | 187        | 83    |
| Control| —                 | 147        | 83    |

Use of RhoA Peptides to Prevent and Treat RSV Infection

Human respiratory syncytial virus is a pneumovirus in the family Paramyxoviridae. It is a nonsegmented negative-strand RNA virus, with a cytoplasmic replication program. The viral nucleocapsid is packaged in a lipoprotein envelope that is acquired from the host cell plasma membrane during budding. The virus has a fusion protein (RSV F) and a G glycoprotein (RSV G). RSV can infect cells as a cell-free virus, but can also spread by syncytium formation between infected cells and uninfected neighboring cells. Membrane fusion is important for both virus entry and for cell-to-cell spread.

RSV G is thought to be the attachment glycoprotein of RSV, although the host cell receptor has never been identified. A cold-passaged B-strain RSV has been shown to infect cells having a deleted G, indicating that RSV F alone may be sufficient for RSV attachment.

RSV F is thought to be tetrameric with four transmembrane virion proteins assembled separately to make up the membrane spikes. RSV G and the small hydrophobic protein (RSV SH) may also be part of the membrane spike structure. The F protein contains a cleaved N terminal signal sequence. The protein requires endoproteolytic cleavage into F1 and F2 to be functional. Results of recent experiments, indicating that whole RhoA enhances viral entry into cells but RhoA peptide from the fusion protein binding region inhibits viral entry, indicate that RhoA is a host cell RSV receptor or coreceptor.

In the present invention, isolated peptides comprising amino acid sequences from the viral fusion protein binding region of the RhoA protein have been shown to inhibit RSV infection by blocking viral entry into susceptible cells both in vivo and in vitro. One such peptide with inhibitory properties comprises the sequence of amino acids 77–95 of the RhoA protein. A smaller inhibitory peptide comprises the sequence of amino acid residues 80–89 of the RhoA protein.

In the present invention, an inhibitory peptide may block viral entry from the cellular environment or may block viral entry into a susceptible cell from an adjacent cell. By inhibiting cell-to-cell spread of the virus, the inhibitory peptide also inhibits syncytium formation.

An inhibitory peptide, peptidomimetic/peptoid, or other mimetic of the present invention may be administered by methods of peptide delivery known to those of skill in the art. Such means may include, but are not limited to, intravenous administration of a solution containing peptide, direct delivery to the respiratory tract, or direct delivery to the preferred site of virus infection. RhoA peptides may be administered to patients who have severe combined immunodeficiency (SCID) or who have undergone immunosuppression during bone marrow transplantation procedures, in order to inhibit cellular infection with RSV either as prevention or treatment. RhoA peptides may be administered for the treatment of bronchiolitis in infants or pneumonia in the elderly. RhoA peptides may be administered as an aerosol nasal spray to block entry of RSV into susceptible cells prior to or subsequent to exposure in persons at risk for infection. This would include a range of individuals from children at high risk due to premature birth, bronchopulmonary dysplasia, or congenital heart disease, to adults at risk of "catching" a cold.

An inhibitory peptide may be used to protect individuals from RSV infection subsequent to exposure to the virus or may be used to inhibit infection in an individual in whom active infection has already been established. In an individual in whom infection has not been established, the peptide will inhibit entry of RSV inoculum into susceptible cells. In an individual in whom infection has been established, the peptide will inhibit syncytium formation and cell-to-cell spread of the virus, as well as inhibit entry into uninfected susceptible cells by virus which has been released into the surrounding tissues and fluids from an infected cell.

The peptides may be delivered by a number of administrative routes. In the case of an individual who has been exposed to, or may subsequently be exposed to, respiratory syncytial virus, a preferred administration route is orally or nasally. The peptides may be combined with a pharmaceutically acceptable carrier for oral or nasal administration. For oral administration, the peptide/carrier may be administered as a mouthwash. For nasal administration, the peptide/carrier may be administered as nasal drops or as an aerosol nasal spray to coat the mucous membranes of the nasopharynx. The peptides may also be combined with a pharmaceutically acceptable carrier to produce an aerosol inhaler for delivery of the peptide to the lungs.

In individuals in whom RSV infection has been established, peptides may be combined with a pharmaceutically acceptable carrier to produce an aerosol inhaler to administer a therapeutic dose of peptide to the tissues of the lung and bronchial passages. In some individuals in whom infection has been established, peptide may be combined with a pharmaceutically acceptable carrier and administered intravenously. Intravenous administration is preferred in certain at-risk individuals in whom infection has been established, particularly the elderly, very young children and infants, children with cystic fibrosis, and children with other respiratory ailments which would predispose them to more severe disease associated with RSV infection. In these individuals, intravenous administration may also be used as a prophylactic measure subsequent to or prior to exposure to RSV.

Previous efforts to produce a vaccine against RSV using inactivated virus have resulted in the production of enhanced disease upon subsequent RSV challenge. Particularly in children, enhanced disease may cause death. Using inhibitory peptide to produce antibody which will block the binding of viral fusion protein to provides a safer, more effective vaccine to protect against RSV infection. The vaccine of the present invention is a peptide vaccine. The peptide may comprise either the inhibitory peptide of the RhoA protein, which has been shown to induce antibodies which will inhibit RSV infection in susceptible cells, or the peptide may comprise a core region of the RhoA-binding domain of the RSV F protein. Administration of the peptide, combined with a pharmaceutically acceptable carrier, as a vaccine to stimulate immunoglobulin production against the peptide results in the production of antibodies with the binding specificity of the viral fusion protein binding domain of the RhoA protein. Administration may also be accomplished by using a recombinant viral vector, such as adenovirus, into which a nucleotide sequence encoding a RhoA or viral fusion protein peptide has been inserted. Antibodies with this binding specificity bind to RSV F and inhibit entry of the virus into susceptible cells in the manner of the RhoA inhibitory peptide.

The inhibitory peptide of the present invention comprises a sufficient number of amino acid residues to promote an immunologic response. Antibodies to viral fusion proteins are commonly produced by the human and mammalian immune systems, indicating that these proteins contain immunogenic epitopes recognized as foreign by the immune system. When peptides are used to immunize animals, they can be administered as free peptides if they are at least 15 residues long. Alternatively, they can be administered as peptide-carrier conjugates, as peptide-liposome conjugates, as peptomers (wherein the immunogen is produced from a series of repeated peptide sequences), or as branched peptides on a core of lysine residues (Van Regenmortel, p. 335).

Many of the uses of the peptides, peptidomimetics and other functional equivalents, and antibodies, described above for RSV, are also useful for prevention and treatment of disease caused by HIV and other viruses, as well.

Use of RhoA Peptides to Prevent and Treat HIV Infection

The inhibitory peptide of the viral fusion protein binding domain of RhoA has also been shown to inhibit infection of susceptible cells by human immunodeficiency virus (HIV-1), which also enters cells by fusion of its membrane with that of a permissive target cell. When MT-2 cell cultures were infected with HIV-1, samples treated with $RhoA_{77-95}$ indicated that treatment with the inhibitory peptide inhibited HIV-1 virus entry into the cells. These results were confirmed by MAGI cell assay, as well as by reverse transcriptase assay, and by visual (microscopic) confirmation that syncytium formation had been inhibited.

Infection with the human immunodeficiency virus has been demonstrated to be sustained by means of continuous viral replication with reinfection of additional host cells. The lentiviruses, such as human immunodeficiency virus, are enveloped viruses. HIV-1 enters cells by fusion of its membrane with that of a permissive target cell. Infected cells then form giant multinucleated cells (syncytia) by fusion of their membranes with those of adjacent cells. HIV-1 proteins expressed on the surface of infected cells induce syncytium formation. Activation of protein kinase C has been found to play a critical role in the process of HIV-1 envelope-dependent syncytia formation (Mohagheghpoour et al.), but the fusion activity associated with the HIV-1 envelope protein is an independent event that does not require expression of the gp120 subunit or the presence of the CD4 receptor (Perez, et al.).

The inventors have demonstrated that HIV-1 utilizes a RhoA-mediated mechanism of entry into susceptible MT-2 cells, since treatment with an inhibitory peptide of the viral fusion protein binding domain of the RhoA protein inhibits viral entry into cells, as well as syncytium formation (indicating inhibition of cell-to-cell spread of the virus). Identification of this fusion receptor, and demonstration of the inhibitory effect of a peptide derived from the RhoA protein, provides a method for inhibiting infection in individuals exposed to human immunodeficiency virus, as well as inhibiting the cell-to-cell spread of virus in those individuals in whom infection has already been established. Methods of using an isolated inhibitory peptide comprising residues from the amino acid sequence of the viral fusion protein binding region of the RhoA protein or the RhoA binding region of gp41, may include, but are not limited to, the methods described below.

RhoA peptide may be used alone or in combination with other anti-viral therapies in the treatment of HIV-1 or HIV-2 infection. RhoA peptide may be used to inhibit initial infection of cells by retrovirus or to inhibit the cell-to-cell spread of retrovirus. RhoA peptide may be used to inhibit HIV binding in infants born to HIV-infected mothers.

Latent HIV reservoirs have been found in CD4+ T cells in infected individuals who have been successfully treated with HAART. Inhibition of cell-to-cell spread in these individuals is critical for the successful treatment of the disease. In these individuals, an inhibitory peptide from the viral fusion protein binding domain of the RhoA protein may be administered concurrently with the HAART regimen. Administration of an inhibitory peptide may, furthermore, be continued subsequent to termination of the HAART program in order to inhibit reactivated virus from cell-to-cell spread from the reservoir CD4+ T cells.

The peptide may be administered intravenously, when combined with a pharmaceutically acceptable carrier, in a therapeutic dosage sufficient to accomplish inhibition of viral infection and spread.

Veazey et al. have recently reported that the intestine appears to be a major target for simian immunodeficiency virus (SIV) replication and the major site of CD4+ T cell loss in early SIV infection. It is clear that HIV targets lymphoid tissue, and the results reported by Veazey indicate that the intestinal tract may be the preferred target for initial infection and replication of HIV, since the proportion of activated memory CD4+ T cells is much greater in the intestinal lamina propria than in the peripheral blood or lymph nodes. The inhibitory peptide of the present invention, if delivered orally in encapsulated (enteric coated) form in a pharmaceutically acceptable carrier, may be released into the mucosa of the intestine to inhibit HIV cell-free and cell-to-cell spread at the site of greatest concentration of susceptible cells. Peptidomimetics imitating the inhibitory effects of RhoA peptides and antibodies may be especially effective for this purpose, since they are more resistant to degradation by digestive enzymes.

A peptide of the present invention may also be used as a prophylactic treatment for individuals who are at risk of HIV infection due to occupational or behavioral risk factors. In health care professionals, an inhibitory peptide may be combined with a pharmaceutically acceptable carrier, such as a saline solution or dermatologic cream, for topical application to the skin at the site of a cut, scratch, or needle prick to inhibit infection of cells by virus inoculum. Administration may also be accomplished by intravenous, oral, or other route. For needle puncture wounds, an inhibitory peptide, combined with a pharmaceutically acceptable carrier, may also be delivered subcutaneously by injection at the wound site. Peptide may be combined with other microbicidal agents in a pharmaceutically acceptable carrier, to prevent HIV infection as well as infection with other infectious agents transmitted from patient to health care worker.

For individuals who are intravenous (IV) drug abusers, peptide may be delivered intravenously to individuals prior to or subsequent to exposure to a source of infection by human immunodeficiency virus.

A peptide of the present invention may be particularly effective for inhibiting sexual transmission of HIV infection. The peptide may be combined with a pharmaceutically acceptable carrier for use by an uninfected individual during sexual intercourse. A pharmaceutically acceptable carrier may include, but not be limited to, a spermicidal jelly, a gel preparation other than a spermicidal jelly, a cream preparation, or a liquid preparation such as a douche. The peptide may also be combined with other microbicidal agents in a pharmaceutically acceptable carrier to provide protection against HIV infection, as well as other sexually transmitted diseases. When used by an infected individual prior to, during or immediately subsequent to sexual intercourse with a potentially infected partner, an inhibitory peptide of the present invention will inhibit entry of, and subsequent infection by, HIV transmitted from the infected individual into the cells of the uninfected sexual partner.

A RhoA inhibitory peptide also provides an immunogen for the production of antibodies which inhibit infection of susceptible cells by HIV. These peptides may be used in vaccines to stimulate in vivo production of antibodies, or, alternatively, may be used to produce anti-RhoA peptide antibodies which can be used for passive immunization to provide inhibition of viral infection in the manner of the RhoA inhibitory peptides. The RhoA binding domain in HIV-1/HIV-2 gp41 may be used as a vaccine to induce the production of antibodies to block viral entry into the cell by binding to the RhoA binding site of the viral fusion protein and competitively inhibiting the binding of the fusion protein to cellular RhoA. The RhoA binding domain of the fusion protein may also be produced as a fusion protein with HIV gp120 for use as a vaccine to produce antibodies with increased capability of neutralizing HIV-1 primary isolates. Dosages and pharmaceutically acceptable carriers have been determined for effective immunogenic effect of gp120 vaccines in human subjects. Similar dosages and carriers are recommended for either HIV-1/HIV-2 gp41 RhoA binding domain peptide vaccine or for HIV gp41/HIV gp120 fusion protein vaccine.

An inhibitory peptide of the present invention has been demonstrated to inhibit infection by respiratory syncytial virus and human immunodeficiency virus. Embodiments described for these viruses, which are both enveloped viruses, are expected to be applicable to other enveloped viruses, as well.

Viruses Sharing Common Cellular Entry Mechanisms may be Inhibited by RhoA Peptides and Antibodies Inhibition of the RhoA-mediated viral entry mechanism described by the present invention provides a common mechanism for the inhibition of entry of other viruses into susceptible cells. Viruses initiate infection by binding to the host cell surface, then penetrate the cell membrane by a specific pathway involving either fusion with the plasma membrane at the cell surface or fusion with vesicle membranes after receptor-mediated endocytosis. An intact actin network is required for efficient entry of herpes simplex virus type 1 and porcine reproductive and respiratory syndrome virus. Nuclear polyhedrosis virus associates with the ends of actin cables as it enters the cytoplasm from endocytic vesicles. HIV entry has also been shown to require an actin-dependent concentration of coreceptors (Iyengar et al.). In fact, an intact actin network appears to be critical to a very early event common to entry into host cells via membrane fusion or receptor-mediated endocytosis (Kizhatil and Albritton).

Viral fusion proteins are also important for viral entry into susceptible cells. Paramyxoviruses, such as RSV, and lentiviruses, such as HIV, enter target cells through a process of pH-independent membrane fusion, which is absolutely critical for virus entry for both cell-free and cell-associated virus. The sequence of the hydrophobic amino terminus of the F1 component of the RSV fusion glycoprotein is similar to that in fusion proteins of lentiviruses (including HIV-1) and paramyxoviruses that share the property of syncytium formation (Gonzales-Scarano et al.). Sequence similarities in these and other virus fusion glycoproteins suggest that diverse groups of enveloped viruses have developed similar structures to enable the fusion of virus and cellular membranes. A heptad repeat pattern is conserved in the amino acid sequence of the fusion glycoprotein of pneumonia virus of mice, respiratory syncytial virus, measles virus, simian virus 5, Newcastle disease virus, Sendai virus, Moloney leukaemia virus, Rous sarcoma virus, Human T cell leukemia virus type 1, human immunodeficiency virus, Visna virus, equine infectious anaemia virus, human spumavirus, transmissible gastroenteritis virus, murine hepatitis virus, infectious bronchitis virus, influenza A virus, influenza B virus, and influenza C virus (Chambers et al.).

Structural similarities between viral fusion proteins also suggest a common membrane fusion mechanism. The ectodomain of the Ebola virus Gp2 glycoprotein folds into a rod-like structure like influenza HA2 and HIV-1 gp41, providing further evidence that viral fusion proteins from diverse families share common structural features (Weissenhorn et al.).

Viruses using the same or similar cellular receptors are not uncommon. Adenovirus type 2, echoviruses 1 and 8, foot-and-mouth disease virus, and coxsackievirus A9 utilize integrins as cellular receptors (Jackson et al.). A human member of the immunoglobulin superfamily has been shown to mediate entry of several alphaherpesviruses, including herpes simplex viruses 1 and 2 (HSV 1 and HSV 2), porcine pseudorabies virus, and bovine herpesvirus 1 (Geraghty et al.). The herpesvirus entry mediator (HVEM) is a member of the tumor necrosis factor receptor superfamily of proteins (Whitbeck et al.), and integrins serve as receptors for a variety of viruses, from adenoviruses to foot-and-mouth disease virus (Jackson, et al.). Echoviruses utilize β2-microglobulin for viral entry (Ward et al.). RhoA and other members of the small G-protein subfamily are highly conserved between species and could therefore serve a role in the membrane fusion mechanism shared among a variety of viruses.

The inhibitory property of the RhoA inhibitory peptide, useful against both RSV infection and HIV infection, may be utilized against more than one virus by blocking viral binding to the RhoA protein using antibody produced by a single vaccine. By inoculating a human or other mammalian subject with any of the isolated peptides of the present invention comprising an immunogenic sequence from the amino acid residues of the RhoA viral fusion protein binding region, the human or other mammalian immune system is stimulated to produce antibodies to the viral fusion protein binding domain of the RhoA protein. By inoculating a human or other mammalian subject with an isolated peptide comprising an immunogenic sequence from the amino acid residues of the RhoA binding region of either RSV F or HIV gp120, or both, the human or other mammalian immune system may be stimulated to produce antibodies to either of these regions, or both. This antibody will have binding specificity to the RhoA binding region of the viral fusion protein, and through its binding to the RhoA binding region of the viral fusion protein will mediate an inhibitory effect on viral infection in the manner of the RhoA viral fusion protein binding region inhibitory peptides of the present invention. RhoA inhibitory peptides, or antibodies mimicking the RhoA inhibitory peptides, therefore, provide a means to provide a single antiviral compound with broad activity against more than one virus-induced disease. Furthermore, because immunoglobulins may be naturally generated by challenge with immunogenic peptide, the RhoA binding region of a viral fusion protein, or an inhibitory peptide derived from the viral fusion protein binding domain of the RhoA protein, provides an ideal candidate for a vaccine with broad activity against a number of viruses.

EXAMPLES

Viruses and Cells

The A2 strain of RSV was provided by Dr. R. Chanock, National Institutes of Health, Bethesda, Md. Virus stocks were prepared as described by Graham et al. HEp-2 cells were maintained in Eagle's minimal essential media (MEM) supplemented with glutamine, gentamicin, penicillin G, and 10% fetal bovine serum.

The MT-2 cell line is a fusion susceptible cell line used as the target cell for the HIV assays. It is a CD4+ T-lymphoblastoid cell line derived from HTLV-1 transformed cord blood lymphocytes (Miyoshi et al.). The subclone of MT-2 cells used for the experiments was a gift from Doug Richman, San Diego Veterans Administration Hospital. MT-2 cells were maintained in RPMI-1640 supplemented with 12% fetal bovine serum (FBC) and 50 mg gentamicin/ml.

Yeast Two-hybrid System

The DNA sequences encoding the respiratory syncytial virus F glycoprotein with and without the transmembrane and cytoplasmic domains were PCR amplified and cloned into EcoRI and BamHI sites of the pAS2-BD vector to generate a fusion between the RSV F protein and the GAL4 DNA-BD. A HeLa cell cDNA library cloned into a pGAD GH vector to generate fusions between proteins encoded by the library cDNAs and the GAL4 AD was obtained from Clontech, Palo Alto, Calif.

The two types of plasmids were cotransformed into the Saccharomyces cerevisiae Y190 reporter host strain. Cotransformants expressing interacting proteins were selected on SD/-HIs/-Leu/-Trp media. To confirm the protein interaction, primary His+ transformants were tested for expression of the second reporter gene using the β-galactosidase assay.

Mammalian Two-hybrid System

The DNA encoding the RSV F protein was cloned into EcoRI and BamHI sites of vector pM to generate fusions of F protein with the GAL4 DNA-BD. The DNA encoding the RhoA protein was cloned into EcoRI and XbaI sites of pVP16 to generate fusions of RhoA protein with the VP16 AD. A third vector, pG5CAT, provided a CAT reporter gene under the control of a GAL4-responsive element and the adenovirus E1b minimal promoter (Clontech). The three vectors were cotransfected into a HEp-2 cell line with Lipofectamine (Gibco BRL), using standard transfection methods. The interaction between the F protein and RhoA was assayed by measuring CAT expression using a CAT ELISA kit (Boehringer Mannheim). The levels of CAT expression were determined by measuring absorbance at 405 nm in a microtiter plate reader (Dynatech Labs).

Enzyme-linked Immunosorbence Assays (ELISA)

Immunoaffinity purified RSV F glycoprotein (provided as a gift by Lederle-Praxis Biologicals, West Henrietta, N.Y.) was diluted to 200 ng/ml in carbonate buffer (pH 9.6). One hundred microliters of diluted F glycoprotein were applied to wells of Immulon II 96-well plates (Nunc, Roskilde, Denmark). Blocking was performed using 3% non-fat dry milk for 1 hour. One hundred microliters of 200 ng/ml concentration RhoA protein and Rac1 protein (CalBiochem, La Jolla, Calif.) were added separately and incubated at room temperature for 2 hours, followed by addition of 1:1000 dilution anti-RhoA and anti-Rac1 monoclonal antibodies (Santa Cruz Biotech, Santa Cruz, Calif.) after washing with PBS-0.1% Tween 20. After 1 hour, plates were washed and a 1:5000 dilution of goat anti-mouse IgG conjugated to horseradish peroxidase was added. After washing, the substrate 3,3',5,5"-tetramethylbenzidine (Sigma) was added and the color intensity was quantified at 405 nm in a Dynatech ELISA reader (Dynatech, Chantilly, Va.).

BIA

The BIA procedure was followed according to the BIAtechnology manual supplied by the manufacturer. A capture molecule, anti-F monoclonal antibody (supplied as a gift from James Crowe) was immobilized, by amine coupling using carbodiimide reaction, on the surface of a carboxymethylated dextran (CM) sensor chip. Immunoaffinity purified F ligand was allowed to flow across the surface of the immobilized monoclonal antibody to capture the F protein. RhoA protein was then applied to flow across the immobilized ligand and the interaction was recorded on the sensorgram as resonance units. Controls were performed using Rac1 as a negative analyte control and an isotype control antibody as an antibody control.

Construction of RhoA Protein Deletion Mutants

Clones encoding different RhoA deletion mutants (FIG. 1) were constructed by PCR amplification. All forward primers contained an EcoRI site and all reverse primers contained an XhoI site. RhoA PCR amplifications were performed using the pGAD GH-RhoA plasmid as a template and 30 cycles with steps of 1 minute at 94° C., 1 minute at 42° C., and 2 minutes at 72° C. PCR products were isolated and purified by agarose gel electrophoresis and digested with EcoRI and XhoI. The resulting fragments were cloned into a pGAD GH vector using the EcoRI and XhoI sites. All constructs were sequenced using a Sequenase® kit (United States Biochemicals) to confirm the sequences. All primers were synthesized by IDT, Coralville, Iowa.

Construction of F Protein Deletion Mutants

Figure 4:
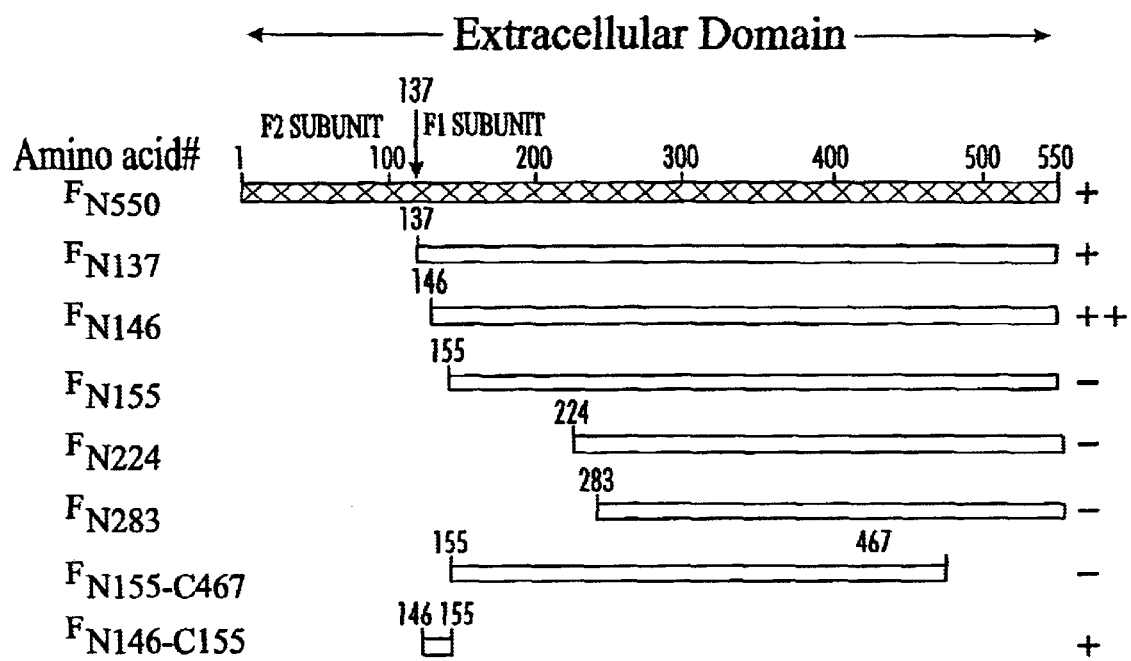
FIG. 4 describes RSV F1 constructs used to perform yeast two-hybrid analysis to determine the location of the RhoA binding domain on RSV F1.

The F deletion mutants (FIG. 4) were constructed by PCR amplification. All forward primers contained an EcoRI site and all reverse primers contained a BamHI site. pGEM-7zF plasmid (Promega) was used as a template and PCR amplified as described above. The resulting fragments were cloned into EcoRI and BamHI sites of the pAS2-BD vector. All constructs were sequenced to confirm the correct sequences.

Construction of gp41 Protein Deletion Mutants

Figure 5:
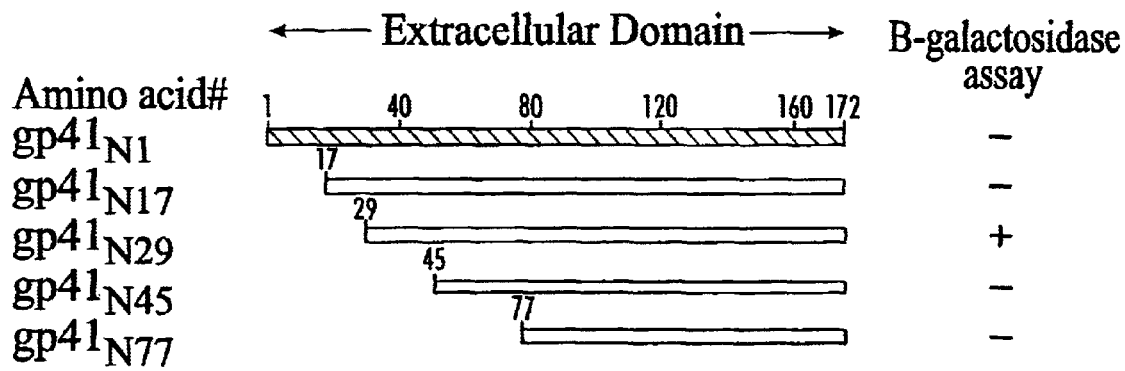
FIG. 5 describes HIV gp41 constructs used to perform yeast two-hybrid analysis to determine the location of the RhoA binding domain on HIV gp41.

The gp41 deletion mutants (FIG. 5) were constructed by PCR amplification. All forward primers contained an EcoRI site and all reverse primers contained a BamHI site. HXB2-env plasmid (provided by Kathleen Page and Dan Littman, National Institutes of Health, Bethesda, Md.) was used as a template and PCR amplified as described above. The resulting fragments were cloned into EcoRI and BamHI sites of the pAS2-BD vector. All the constructs were sequenced to confirm the sequences.

Inhibition Assays

Peptides used in the inhibition assays were synthesized by Research Genetics, Inc., Huntsville, Ala. Peptides were incubated with 103 plaque forming units per milliliter (pfu/ml) of RSV at concentrations of 5 and 10 mg/ml for one hour on ice. The virus/peptide suspension was then added to HEp-2 cells in 96-well culture plates. After 3 days, plates were fixed with methanol and RSV-specific immunoperoxidase staining was performed in the manner described by Crowe et al.

Human cDNAs Encode Proteins which Interact with RSVF Protein

Human cDNAs that encoded proteins which could interact with the RSV F protein were identified using the yeast two-hybrid protein interaction trap. The screened library consisted of the Gal4 transcription activation domain fused to cDNA sequences derived from a human HeLa cell line. Eight clones were identified which encoded Gal4 AD-prey fusion proteins that specifically interacted with the Gal4 BD-F bait protein specifically. Computer analysis of available sequence databases identified proteins displaying significant homologies to the predicted ribosomal S20, RhoA, growth factor receptor and plasmid sequences. Only the RhoA protein clone, of the 8 clones, was found to bind the F bait protein specifically. This result was determined by reversing the identities of the bait and prey proteins so that the bait protein was expressed as a Gal4 AD-F fusion while the RhoA protein was expressed as a Gal4 BD-RhoA fusion protein, and reassaying completely isolated colonies containing segregated Gal4 AD-RhoA and Gal4 BD-F plasmids to verify the LacZ+ phenotype. The cDNA clone of RhoA contained 1777 nucleotide bases with a predicted open reading frame of 193 amino acids.

Interaction of RhoA with F Protein Demonstrated in Mammalian Cells

Two-hybrid analysis in a mammalian system was performed using DNA cloning vectors pM and pVP16 (Clontech Laboratories, Palo Alto, Calif.) to generate fusions of protein F with the GAL4 DNA-BD and fusions of protein RhoA with the VP16 AD, respectively. A third vector, pG5CAT, provided the GAL4 binding site, the minimal promoter of the adenovirus E1b, and the chloramphenicol acetyl transferase (CAT) reporter gene.

RhoA Peptide Blocks Binding of RSV to HEp-2 Cells

A 43 amino acid region of the RhoA protein, comprising amino acids 67–109, has been found to specifically bind to the fusion domain of the respiratory syncytial virus F glycoprotein, using the yeast two-hybrid system (Pastey et al.). Three overlapping 19 amino acid peptides were made which spanned the region shown to bind to the RSV F protein. These peptides from the RhoA protein sequence included amino acids 67–85, 77–95, and 87–105, respectively.

The peptides were incubated with 103 plaque forming units per milliliter (pfu/ml) of RSV at concentrations of 5 mg/ml and 10 mg/ml for one hour at room temperature. One hundred microliters of the suspension was then added to HEp-2 cells in 96-well microtiter plates. Plates were incubated for three days, with subsequent methanol fixation and immunoperoxidase staining using RSV-specific antibody.

RhoA peptide comprising amino acids 77–95 (RhoA$_{77-95}$) completely blocked plaque formation (FIG. 2), while peptides comprising RhoA amino acids 67–85 (RhoA$_{67-85}$) and amino acids 87-105 (RhoA$_{87-105}$) were found to provide no inhibition of plaque formation, when compared to phosphate-buffered saline (PBS) treated controls. That this lack of plaque formation is correlated with inhibition of RSV entry into the cells is indicated by the fact that no antigen-positive cells were found when analyzed by immunoperoxidase staining.

RhoA Peptide Inhibits Cell-to-cell Spread of RSV

Cell-to-cell spread of RSV was also shown to be inhibited by the addition of RhoA$_{77-95}$. RhoA$_{77-95}$ was added to cells in aliquots of 5 mg/ml at timed intervals after RSV adsorption, and the infected HEp-2 cell monolayers were evaluated three days after the addition of RhoA peptide. Peptide was added between 4 and 24 hours after viral adsorption. Peptide added at 4 hours reduced the number of virus infected cells and limited infection to single cells. Peptide added at 20 or 24 hours post-adsorption inhibited syncytia formation, limiting syncytium formation to a few cells, rather than the larger syncytia normally seen in RSV infection.

The binding interaction of RhoA and RSV F protein was further defined by adding a series of overlapping 10 amino acid peptides to the HEp-2 cell medium. Among these 10 amino acid peptides were RhoA$_{77-86}$, RhoA$_{80-89}$, and RhoA$_{83-92}$. Addition of RhoA$_{83-92}$ or RhoA$_{77-86}$ did not block syncytium formation, while RhoA$_{80-89}$ completely blocked RSV entry into the HEp-2 cells, suggesting that the key binding domain lies between RhoA amino acids 80 and 89.

Treatment with RhoA Peptide Reduces the Severity of RSV Infection

BALB/c mice were infected with $10^7$ plaque forming units (pfu) of RSV, using a disease model previously described by Graham et al. Using this model, the RSV-induced clinical syndrome can be detected by day 4 or 5 post-infection. Mice were given 500 μg of RhoA$_{77-95}$ in 100 ml of phosphate buffered saline (PBS) intranasally either at the time of RSV challenge or on day 4 after RSV infection. Mice treated at the time of virus challenge had no discernable illness or weight loss. Mice treated at day 4 had markedly diminished signs of illness, and slight reduction in weight loss relative to PBS-treated controls. RSV replication was also diminished in the lung, as indicated by plaque assays on lungs from day 5 after RSV challenge. These assays indicated that treatment with RhoA$_{77-95}$ at the time of infection decreased RSV titers by over 100-fold, while treatment with RhoA$_{77-95}$ on day 4 reduced titers by more than 10-fold, as shown in Table 2.

TABLE 2

| Day of Peptide Treatment | Day 5 RSV Titer (Log10 pfu/gram lung ± S.D.) |
| --- | --- |
| 0 | 3.7 ± 0.3 |
| 4 | 4.7 ± 0.3 |
| None | 6.0 ± 0.3 |

The Effects of RhoA Peptide are Not Limited to Inhibition of RSV Infection

RhoA$_{77-95}$ was also added to HEp-2 cells in conjunction with parainfluenza virus 3 (PIV3) as infectious agent, as well as MT-2 cells, in conjunction with human immunodeficiency virus 1 (HIV-1) as infectious agent. Both viruses are known to cause the formation of syncytia during infection. Using RhoA$_{77-95}$, syncytium formation was inhibited in both models.

Figure 2:
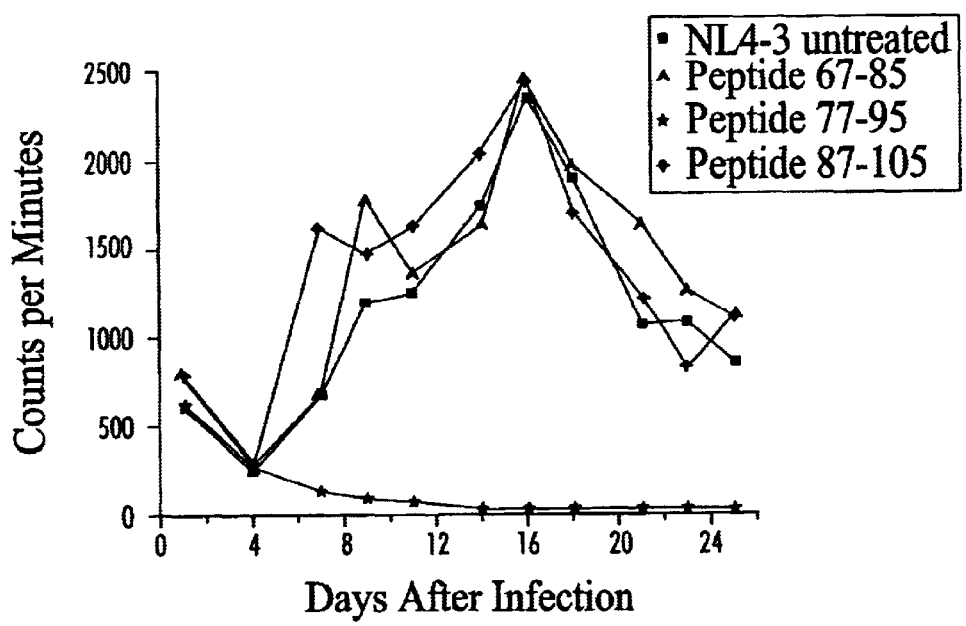
FIG. 2 is a graph illustrating the results of a reverse transcriptase (RT) assay performed on supernatants from unwashed MT-2 cells infected with 200 ng of HIV-1 and treated with peptide. Controls infected with HIV-1 NL4-3 and untreated (NL4-3 untreated). The vertical axis represents units of RT activity, while the horizontal axis represents days post-infection. Identity of peptides used is indicated by the symbols noted in the box at the top of the graph.
Figure 3:
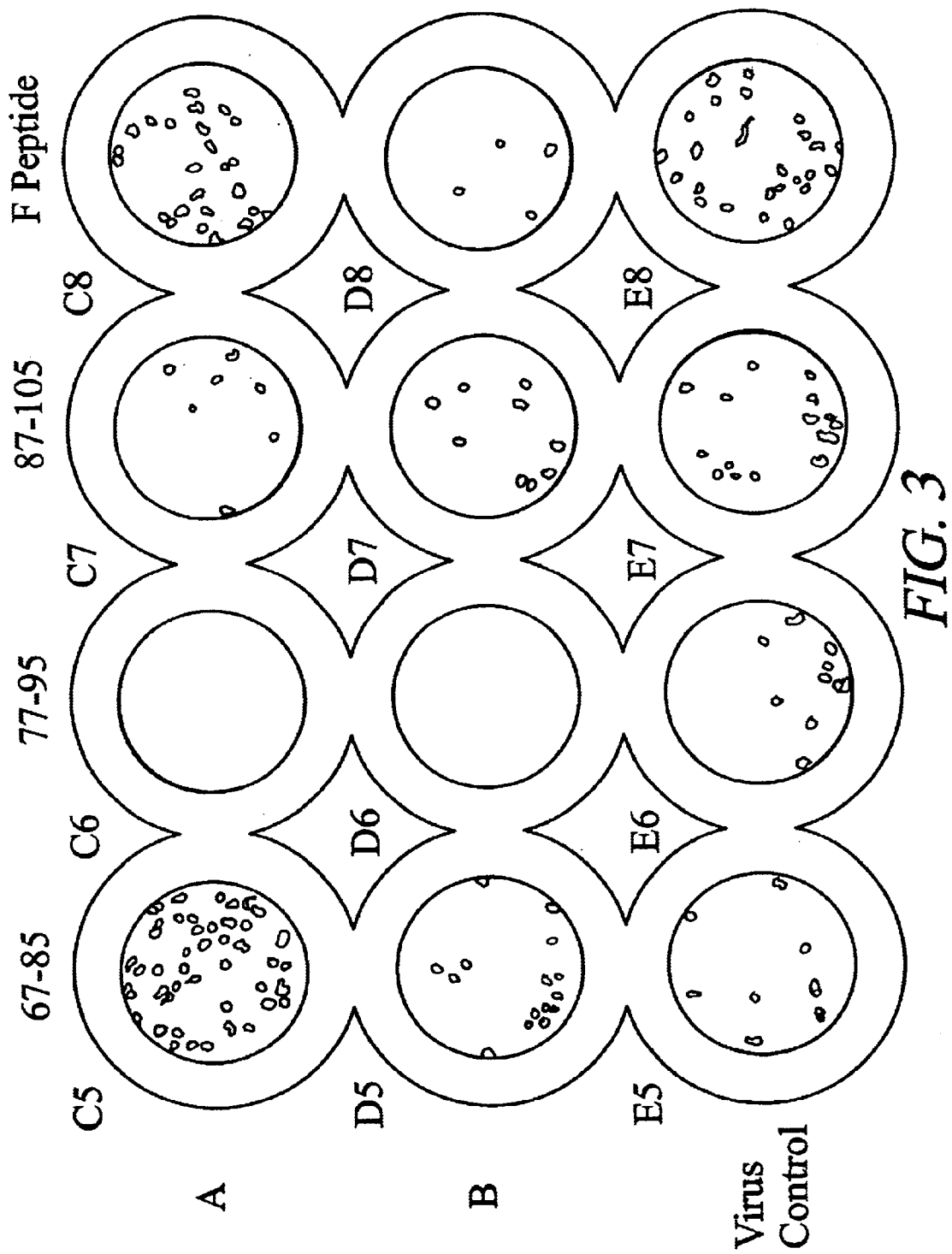
FIG. 3 illustrates plaque formation in cells grown on microtiter plates and treated with peptide in conjunction with virus inoculum. Wells labeled as C5 and D5 were treated with the RhoA$_{67-85}$ peptide. Wells labeled as C7 and D7 were treated with RhoA$_{87-105}$ peptide. E series wells were virus controls, receiving virus inoculum without peptide treatment. Wells C8 and D8 received virus inoculum and the F peptide as control. Plaque formation was inhibited in wells C6 and D6, representing cells treated with RhoA$_{77-95}$ peptide in conjunction with virus inoculum.

MT-2 cell cultures were infected with either 20 ng or 200 ng of HIV-1 in 24-well microtiter plates. Cells were either washed after a 1 hour virus adsorbtion, or left unwashed. Cells infected with HIV-1, as well as infected cells treated with RhoA$_{67-85}$ or RhoA$_{87-105}$, produced visible syncytia by day 4, and were completely destroyed by day 14. No syncytium formation was detected through day 21 post-infection in the HIV-1 infected cells treated with RhoA$_{77-95}$. Reverse transcriptase (Rt) and p24 assays were performed on serial harvests of culture supernatants. The results of these assays confirm that HIV-1 replication is inhibited by RhoA$_{77-95}$ (FIG. 2). Initially, a low level of RT activity is detectable in the wells containing cells infected with HIV-1 and treated with RhoA$_{77-95}$, due to residual virus from the initial inoculum. However, by day 4 reverse transcriptase activity is undetectable and remains undetectable through day 21 post-infection.

Anti-RhoA$_{77-95}$ Antibodies also Inhibit Virus Entry

Polyclonal antibodies against RhoA$_{77-95}$ were raised in rabbit, using standard techniques. Anti-RhoA$_{77-95}$ was then tested for its ability to inhibit virus entry and cell-to-cell spread after infection. Antibody dilutions of 1:100, 1:150, 1:200, 1:300, and 1:600 were prepared and added to respective HEp-2 cell monolayers in 96-well plates. RSV was added to each well at a concentration of 1000 pfu/ml. After 3 days incubation, plates were fixed with methanol and stained using RSV-specific immunoperoxidase staining, as described by Crowe, et al. No plaques were noted in wells treated with 1:100 and 1:150 dilutions of antibody. Wells treated with antibody dilutions of 1:200, 1:300, and 1:600 contained 10, 21, and 29 plaques, respectively. Preimmune controls contained greater than 30 plaques per well, with syncytia covering the entire well.

Inhibition of HIV virus entry into cells by RhoA$_{77-95}$ has also been demonstrated by MAGI cell assay, using β-galactosidase activity as endpoint.

The following references, to the extent that they provide details supplementary to those set forth herein, are specifically incorporated herein by reference.

Agosto, et al. (1998), "AIDS Vaccine Development," *Science* 280: 803–807.

Balter (1998), "AIDS Researchers Negotiate Tricky Slopes of Science," *Science* 280: 825–826.

Chambers, et al. (1990), "Heptad Repeat Sequences are Located Adjacent to Hydrophobic Regions in Several Types of Virus Fusion Glycoproteins," *J. Gen. Virol.* 71: 3075–3080.

Chargelegue, et al. (1998), "A Peptide Mimic of a Protective Epitope of Respiratory Syncytial Virus Selected from a Combinatorial Library Induces Virus-Neutralizing Antibodies and Reduces Viral Load In vivo," *J. Virol.* 72(3): 2040–2046.

Chen, et al. (1993), "Mutational Analysis of the Leucine Zipper-like Motif of the Human Immunodeficiency Virus Type 1 Envelope Transmembrane Glycoprotein," *J. Virol* 67: 3615–3619.

Chen, et al. (1994), "Functional Role of the Zipper Motif Region of Human Immunodeficiency Type 1 Transmembrane Protein gp41," *J. Virol* 68: 2002–2010.

Chun, et al. (1997), "Presence of an Inducible HIV-1 Latent Reservoir During Highly Active Retroviral Therapy," *Proc. Natl. Acad. Sci. USA* 94: 13193–13197.

Crowe J E Jr, et al. (1998), "Isolation of a second recombinant human respiratory syncytial virus monoclonal antibody fragment (Fab RSVF2–5) that exhibits therapeutic efficacy in vivo," *J Infect Dis.* 177(4): 1073–1076.

Downward, J. (1990), "The Ras Superfamily of Small GTP-binding proteins," *TIBS* 15: 469–472.

Drivas, et al. (1991), "Evolutionary Grouping of the Ras-Protein Family," *Biochem. Biophys. Res. Commun.* 176 (3): 1130–1135.

Frangione, et al. (1993), "Solubilization and Purification of Enzymatically Active Glutathione S-Transferase (pGEX) Fusion Proteins," *Anal. Biochem.* (210) 179–187.

Geraghty, et al. (1998), "Entry of Alphaherpesviruses Mediated by Poliovirus Receptor-Related Protein 1 and Poliovirus Receptor," *Science* 280: 1618–1620.

Gonzales-Scarano, et al. (1987), "Sequence Similarities Between Human Immunodeficiency Virus gp41 and Paramyxovirus Fusion Proteins," *AIDS Res. Hum. Retrouiruses* 3(3): 245–252.

Graham, et al. (1988), "Primary Respiratory Syncytial Virus Infection in Mice," *J. Med. Virol* 26: 153–162.

Hall (1998), "Rho GTPases and the Actin Cytoskeleton," *Science* 279: 509–514.

Houghten, et al. (1991), "Generation and Use of Synthetic Peptide Combinatorial Libraries for Basic Research and Drug Discovery," *Nature* 354: 84–86.

Iyengar, et al. (1998), "Actin-Dependent Receptor Colocalization Required for Human Immunodeficiency Virus Entry into Host Cells," *J. Virol.* 72: 5251–5255.

Lam, et al., (1991), "A New Type of Synthetic Peptide Library for Identifying Ligand-binding Activity," *Nature* 354: 82–84.

Lam, et al., (1998), "Application of 'One-Bead One-Compound' Combinatorial Library Methods in Signal Transduction Research," *Life Sciences* 62 (17/18): 1577–1583.

Machesky, L. et al. (1997), "Role of Actin Polymerization and Adhesion to Extracellular Matrix in Rac- and Rho-induced Cytoskeletal Organization," *J. Cell Biol.*: 913–926.

Miyoshi, et al. (1981), "Type C Virus Particles in a Cord T-cell Line Derived by Co-cultivating Normal Human Cord Leukocytes and Human Leukaemic T Cells," *Nature* 294: 770–771.

Mohagheghpoour, et al. (1991), "Early Activation Events Render T Cells Susceptible to HIV-1-induced Syncytia Formation," *J. Biol. Chem.* 266(11): 7233–7238.

Narumiya, S. (1996), "The Small GTPase Rho: Cellular Functions and Signal Transduction," *J. Biochem.* 120: 215–228.

Owen, et al. (1998), "Genetically Divergent Strains of Human Immunodeficiency Virus Type 2 Use Multiple Coreceptors for Viral Entry," *J. Virol.* 72(7): 5425–5432.

Perez, et al. (1992), "The Transmembrane Glycoprotein of Human Immunodeficiency Virus Type 1 Induces Syncytium Formation in the Absence of the Receptor Binding Glycoprotein," *J. Virol.* 66(7): 4134–4143.

---

SEQUENCE LISTING

```
<160> NUMBER OF SEQ ID NOS: 2

<210> SEQ ID NO 1
<211> LENGTH: 19
<212> TYPE: PRT
<213> ORGANISM: Homo sapiens

<400> SEQUENCE: 1

Thr Asp Val Ile Leu Met Cys Phe Ser Ile Asp Ser Pro Asp Ser Leu
1               5                   10                  15

Glu Asn Ile

<210> SEQ ID NO 2
<211> LENGTH: 10
<212> TYPE: PRT
<213> ORGANISM: Homo sapiens

<400> SEQUENCE: 2

Ile Leu Met Cys Phe Ser Ile Asp Ser Pro
1               5                   10
```

---

Jackson, et al. (1997), "Arginine-Glycine-Aspartic Acid-Specific Binding by Foot-and-Mouth Disease Viruses to the Purified Integrin avb3 In vitro," *J. Virol.* 71(11): 8357–8361.

Kizhatil, K. and Albritton, L. (1997), "Requirements for Different Components of the Host Cell Cytoskeleton Distinguish Ecotropic Murine Leukemia Virus Entry via Endocytosis from Entry via Surface Fusion," *J. Virol.* 71(10): 7145–7156.

Kyte, et al. (1982), "A Simple Method for Displaying the Hydropathic Character of a Protein," *J. Mol. Biol.* 157: 105–132.

We claim:

1. An isolated peptide comprising the amino acid sequence Ile-Leu-Met-Cys-Phe-Ser-Ile-Asp-Ser-Pro (SEQ. I.D. NO. 2).

2. The peptide of claim 1, wherein the peptide comprises the amino acid sequence Thr-Asp-Val-Ile-Leu-Met-Cys-Phe-Ser-Ile-Asp-Ser-Pro-Asp-Ser-Leu-Glu-Asn-Ile (SEQ. I.D. NO. 1).

* * * * *